United States Patent
Sharonov

(10) Patent No.: US 9,662,165 B2
(45) Date of Patent: *May 30, 2017

(54) DEVICE AND METHOD FOR HEAT-SENSITIVE AGENT APPLICATION

(71) Applicant: COVIDIEN LP, Mansfield, MA (US)

(72) Inventor: Alexey Sharonov, Bethany, CT (US)

(73) Assignee: COVIDIEN LP, Mansfield, MA (US)

( * ) Notice: Subject to any disclaimer, the term of this patent is extended or adjusted under 35 U.S.C. 154(b) by 432 days.

This patent is subject to a terminal disclaimer.

(21) Appl. No.: 13/942,883

(22) Filed: Jul. 16, 2013

(65) Prior Publication Data

US 2014/0094793 A1    Apr. 3, 2014

Related U.S. Application Data

(60) Provisional application No. 61/708,905, filed on Oct. 2, 2012.

(51) Int. Cl.
*A61B 18/12* (2006.01)
*A61B 18/14* (2006.01)
(Continued)

(52) U.S. Cl.
CPC ............ *A61B 18/1233* (2013.01); *A61B 8/08* (2013.01); *A61B 8/085* (2013.01); *A61B 8/481* (2013.01);
(Continued)

(58) Field of Classification Search
CPC ..... A61B 18/12; A61B 18/1233; A61B 18/14; A61B 18/1477; A61B 18/18;
(Continued)

(56) References Cited

U.S. PATENT DOCUMENTS

| D223,367 S | 4/1972 | Kountz |
|---|---|---|
| D263,020 S | 2/1982 | Rau, III |

(Continued)

FOREIGN PATENT DOCUMENTS

| CN | 1103807 | 6/1995 |
|---|---|---|
| DE | 390937 | 3/1924 |

(Continued)

OTHER PUBLICATIONS

Huang. et al. "Heat-sensitive microbubbles for intraoperative assessment of cancer ablation margins", Biomaterials 31 (2010) 1278-1286.*

(Continued)

*Primary Examiner* — Michael Peffley
*Assistant Examiner* — Khadijeh Vahdat

(57) ABSTRACT

A method of directing energy to tissue includes the initial steps of determining target tissue location and/or target tissue margins, positioning an ablation device for delivery of energy to target tissue, and introducing a material having a shape into a tissue region to be monitored. The material is adapted to change echogenic properties in response to heat. The method also includes the steps of applying energy to the ablation device, monitoring the material on a monitor, determining an echogenic response of the material, and terminating ablation if it is determined that the echogenic response of the material is outside a predetermined target tissue threshold.

15 Claims, 10 Drawing Sheets

(51) Int. Cl.
*A61B 8/08* (2006.01)
*A61B 18/18* (2006.01)
*A61B 17/00* (2006.01)
*A61B 18/00* (2006.01)
*A61B 90/00* (2016.01)

(52) U.S. Cl.
CPC ...... *A61B 18/1477* (2013.01); *A61B 18/1815* (2013.01); *A61B 8/5223* (2013.01); *A61B 2017/00106* (2013.01); *A61B 2018/00023* (2013.01); *A61B 2018/0072* (2013.01); *A61B 2018/00642* (2013.01); *A61B 2018/00702* (2013.01); *A61B 2018/00714* (2013.01); *A61B 2018/00755* (2013.01); *A61B 2018/00761* (2013.01); *A61B 2018/00767* (2013.01); *A61B 2018/00791* (2013.01); *A61B 2018/143* (2013.01); *A61B 2090/378* (2016.02); *A61B 2090/3925* (2016.02)

(58) Field of Classification Search
CPC ...... A61B 18/1815; A61B 2018/00023; A61B 2018/00642; A61B 2018/00702; A61B 2018/00714; A61B 2018/0072; A61B 2018/00755; A61B 2018/00761; A61B 2018/00767; A61B 2018/00791; A61B 2018/143; A61B 8/08; A61B 8/085; A61B 8/481; A61B 8/5223; A61B 2019/5276; A61B 2019/5425
USPC .................................................. 606/33–41
See application file for complete search history.

(56) References Cited

U.S. PATENT DOCUMENTS

| | | | |
|---|---|---|---|
| D266,842 S | 11/1982 | Villers et al. | |
| D278,306 S | 4/1985 | McIntosh | |
| D295,893 S | 5/1988 | Sharkany et al. | |
| D295,894 S | 5/1988 | Sharkany et al. | |
| 4,869,259 A | 9/1989 | Elkins | |
| 5,370,675 A | 12/1994 | Edwards et al. | |
| D354,218 S | 1/1995 | Van de Peer | |
| 5,560,712 A | 10/1996 | Kleinerman | |
| 6,002,968 A | 12/1999 | Edwards | |
| D424,693 S | 5/2000 | Pruter | |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| D487,039 S | 2/2004 | Webster et al. | |
| D496,997 S | 10/2004 | Dycus et al. | |
| 6,802,839 B2 | 10/2004 | Behl | |
| D499,181 S | 11/2004 | Dycus et al. | |
| 7,065,394 B2 | 6/2006 | Hobot et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,220,259 B2 | 5/2007 | Harrington et al. | |
| D564,662 S | 3/2008 | Moses et al. | |
| 7,387,626 B2 | 6/2008 | Edwards et al. | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| D634,010 S | 3/2011 | DeCarlo | |
| D681,810 S | 5/2013 | DeCarlo | |
| 9,439,712 B2 * | 9/2016 | Sharonov | A61B 18/12 |
| 2002/0087151 A1 | 7/2002 | Mody et al. | |
| 2003/0083654 A1 | 5/2003 | Chin et al. | |
| 2006/0224156 A1 | 10/2006 | Arts et al. | |
| 2007/0173680 A1 | 7/2007 | Rioux et al. | |
| 2007/0287996 A1 | 12/2007 | Rioux | |
| 2008/0125775 A1 | 5/2008 | Morris | |
| 2008/0183165 A1 | 7/2008 | Buysse et al. | |
| 2010/0249771 A1* | 9/2010 | Pearson et al. | 606/34 |
| 2011/0054459 A1 | 3/2011 | Peterson | |
| 2011/0301590 A1 | 12/2011 | Podhajsky et al. | |
| 2013/0041251 A1* | 2/2013 | Bailey | A61B 5/076 600/424 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |

(56) References Cited

FOREIGN PATENT DOCUMENTS

| JP | 07265328 | | 10/1995 |
|---|---|---|---|
| JP | 08056955 | | 3/1996 |
| JP | 08252263 | | 10/1996 |
| JP | 09000492 | | 1/1997 |
| JP | 09010223 | | 1/1997 |
| JP | 11244298 | | 9/1999 |
| JP | 2000342599 | | 12/2000 |
| JP | 2000350732 | | 12/2000 |
| JP | 2001003776 | | 1/2001 |
| JP | 2001008944 | | 1/2001 |
| JP | 2001029356 | | 2/2001 |
| JP | 2001037775 | | 2/2001 |
| JP | 2001128990 | | 5/2001 |
| JP | 2001231870 | | 8/2001 |
| JP | 2008142467 | | 6/2008 |
| KR | 20070093068 | | 9/2007 |
| KR | 20100014406 | | 2/2010 |
| KR | 20120055063 | | 5/2012 |
| SU | 166452 | | 11/1964 |
| SU | 401367 | | 11/1974 |
| SU | 727201 | | 4/1980 |
| WO | 8702769 | A1 | 5/1987 |
| WO | WO00/36985 | | 6/2000 |
| WO | WO2008/144341 | | 11/2008 |
| WO | WO2010/035831 | | 4/2010 |
| WO | 2010102117 | A1 | 9/2010 |
| WO | 2012071388 | A2 | 5/2012 |

OTHER PUBLICATIONS

European Search Report, Application No. EP 13 18 6382 dated Feb. 27, 2014.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
U.S. Appl. No. 13/957,087, filed Aug. 1, 2013, Brannan.
U.S. Appl. No. 13/973,543, filed Aug. 22, 2013, Orszulak.
U.S. Appl. No. 14/011,414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
U.S. Appl. No. 14/017,995, filed Sep. 4, 2013, Brannan.
U.S. Appl. No. 14/018,081, filed Sep. 4, 2013, Brannan.
U.S. Appl. No. 08/136,098, filed Oct. 14, 1993, Roger A. Stern.
U.S. Appl. No. 08/483,742, filed Jun. 7, 1995, Roger A. Stern.

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/ Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With The LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds In Urology 1999, vol. 1, Issue 4, pp. 10-17.

(56) References Cited

OTHER PUBLICATIONS

Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am, J. MI, Jan. Mar. 1964, pp. 16-27.
Goldberg et al., "Image-guided Radiofrequency Tumor Ablation: Challenges and Opportunities—Part 1", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes To Model Electrical Heating And Non•LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College Of Surgeons (ACS) Clinic La Congress Poster (2000).
Johnson et al., "New Low-Profile Applicators for Local Heating ofTissues", IEEE Transactions on Biomedical Engineering, vol., BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparoscopic Surgery, Sales/Product Literature, Jan. 2004.

Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Pallazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.

(56) References Cited

OTHER PUBLICATIONS

Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology , "Overcoming the Challenge" located at: <http://www.urologix.com/medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.

\* cited by examiner

DEVICE AND METHOD FOR HEAT-SENSITIVE AGENT APPLICATION

CROSS REFERENCE TO RELATED APPLICATION

The present application claims the benefit of and priority to U.S. Provisional Application Ser. No. 61/708,905, filed on Oct. 2, 2012, the entire contents of which are incorporated herein by reference.

BACKGROUND

1. Technical Field

The present disclosure relates to systems, devices and methods for performing a medical procedure. More particularly, the present disclosure relates to devices and methods for heat-sensitive agent (and/or drug agent) application, electrosurgical systems including the same, and methods of directing energy to tissue using the same.

2. Discussion of Related Art

Electrosurgery is the application of electricity and/or electromagnetic energy to cut, dissect, ablate, coagulate, cauterize, seal or otherwise treat biological tissue during a surgical procedure. When electrical energy and/or electromagnetic energy is introduced to tissue, the energy-tissue interaction produces excitation of molecules, creating molecular motion that results in the generation of heat. Electrosurgery is typically performed using a handpiece including a surgical instrument (e.g., end effector, ablation probe, or electrode) adapted to transmit energy to a tissue site during electrosurgical procedures, an electrosurgical generator operable to output energy, and a cable assembly operatively connecting the surgical instrument to the generator.

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue. The application of ultrasound imaging is one of the cost-effective methods often used for tumor localization and ablation device placement.

There are a number of different types of apparatus that can be used to perform ablation procedures. Typically, apparatus for use in ablation procedures include a power generating source, e.g., a microwave or radio frequency (RF) electrosurgical generator, that functions as an energy source, and a surgical instrument (e.g., microwave ablation probe having an antenna assembly) for directing the energy to the target tissue. The generator and surgical instrument are typically operatively coupled by a cable assembly having a plurality of conductors for transmitting energy from the generator to the instrument, and for communicating control, feedback and identification signals between the instrument and the generator.

Using electrosurgical instruments to ablate, seal, cauterize, coagulate, and/or desiccate tissue may result in some degree of thermal injury to surrounding tissue. For example, electrosurgical desiccation may result in undesirable tissue damage due to thermal effects, wherein otherwise healthy tissue surrounding the tissue to which the electrosurgical energy is being applied is thermally damaged by an effect known in the art as "thermal spread". During the occurrence of thermal spread, excess heat from the operative site can be directly conducted to the adjacent tissue and/or the release of steam from the tissue being treated at the operative site can result in damage to the surrounding tissue. The duration of the activation of the generator is directly related to the heat produced in the tissue. The greater the heat produced, the more the potential for thermal spread to adjacent tissues.

Currently available systems and methods for controlling an electrosurgical generator during electrosurgery may include a clinician monitoring and adjusting, as necessary, the amount of energy delivered to a tissue site through current, voltage, impedance, and/or power measurements such that an appropriate tissue effect can be achieved at the tissue site with minimal collateral damage resulting to adjacent tissue. These systems and/or methods typically require a clinician to translate the desired tissue effect to a power setting on an electrosurgical generator and, if necessary, adjust the power setting to compensate for tissue transformations (e.g., desiccation of tissue) associated with the electrosurgical procedure such that a desired tissue effect may be achieved.

It can be difficult to determine the size of an ablated zone and/or to assess the margins of ablated tissue. As can be appreciated, limiting the possibility of thermal spread or the like during an electrosurgical procedure reduces the likelihood of unintentional and/or undesirable collateral damage to surrounding tissue structures which may be adjacent to an intended treatment site. Controlling and/or monitoring the depth of thermal spread during an electrosurgical procedure may aid a clinician in assessing tissue modification and/or transformation during the electrosurgical procedure.

Medical imaging has become a significant component in the clinical setting and in basic physiology and biology research, e.g., due to enhanced spatial resolution, accuracy and contrast mechanisms that have been made widely available. Medical imaging now incorporates a wide variety of modalities that noninvasively capture the structure and function of the human body. Such images are acquired and used in many different ways including medical images for diagnosis, staging and therapeutic management of malignant disease.

Because of their anatomic detail, computed tomography (CT) and magnetic resonance imaging (MRI) are suitable for, among other things, evaluating the proximity of tumors to local structures. CT and MRI scans produce two-dimensional (2-D) axial images, or slices, of the body that may be viewed sequentially by radiologists who visualize or extrapolate from these views actual three-dimensional (3-D) anatomy.

Medical image processing, analysis and visualization play an increasingly significant role in disease diagnosis and monitoring as well as, among other things, surgical planning and monitoring of therapeutic procedures. Unfortunately, tissue heating and thermal damage does not create adequate contrast in ultrasound images to allow determination of the size of an ablated zone and assessment of the margins of ablated tissue.

SUMMARY

A continuing need exists for systems, devices and methods for controlling and/or monitoring real-time tissue effects to improve patient safety, reduce risk, and/or improve patient outcomes. There is a need for intraoperative techniques for ablation margin assessment and feedback control.

According to an aspect of the present disclosure, a method of directing energy to tissue is provided. The method includes the initial steps of determining target tissue location and/or target tissue margins, positioning an ablation device for delivery of energy to target tissue, and introducing a material having a shape into a tissue region to be monitored. The material is adapted to change echogenic properties in response to heat. The method also includes the steps of applying energy to the ablation device, monitoring the material on a monitor, determining an echogenic response of the material, and terminating ablation if it is determined that the echogenic response of the material is outside a predetermined target tissue threshold.

According to another aspect of the present disclosure, a method of directing energy to tissue is provided. The method includes the initial steps of determining target tissue location and/or target tissue margins, positioning an energy applicator for delivery of energy to target tissue, and positioning one or more shaped portions of a heat-sensitive material into tissue. The one or more shaped portions of the heat-sensitive material are adapted to change echogenic properties in response to heat. The method also includes the steps of transmitting energy from an electrosurgical power generating source through the energy applicator to the target tissue, acquiring data representative of one or more images including data representative of a response of the one or more shaped portions of the heat-sensitive material to the heat generated by the energy transmitted to the target tissue, and determining at least one operating parameter associated with the electrosurgical power generating source based at least in part on the response of the one or more shaped portions of the heat-sensitive material.

In any one of the aspects, the one or more operating parameters associated with the electrosurgical power generating source may be selected from the group consisting of temperature, impedance, power, current, voltage, mode of operation, and duration of application of electromagnetic energy.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second).

As it is used in this description, "ablation procedure" generally refers to any ablation procedure, such as microwave ablation, radio frequency (RF) ablation or microwave ablation assisted resection. As it is used in this description, "energy applicator" generally refers to any device that can be used to transfer energy from a power generating source, such as a microwave or RF electrosurgical generator, to tissue. As it is used in this description, "transmission line" generally refers to any transmission medium that can be used for the propagation of signals from one point to another. As it is used in this description, "fluid" generally refers to a liquid, a gas or both.

BRIEF DESCRIPTION OF THE DRAWINGS

Objects and features of the presently-disclosed devices for heat-sensitive agent (and/or drug agent) application, electrosurgical systems including the same, and methods of directing energy to tissue using the same will become apparent to those of ordinary skill in the art when descriptions of various embodiments thereof are read with reference to the accompanying drawings, of which.

DETAILED DESCRIPTION

Figure 1:
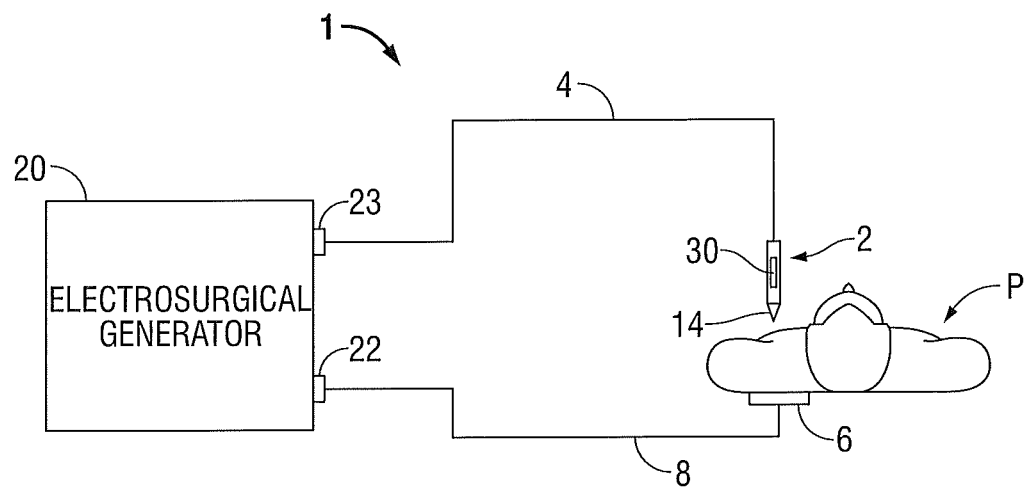
FIG. 1 is a schematic diagram of an electrosurgical system, such as a monopolar electrosurgical system, according to an embodiment of the present disclosure.

Hereinafter, embodiments of the presently-disclosed device and method for heat-sensitive agent application, electrosurgical system including the same, and method of directing energy to tissue using the same are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the device, or component thereof, closer to the user and the term "distal" refers to that portion of the device, or component thereof, farther from the user.

This description may use the phrases "in an embodiment," "in embodiments," "in some embodiments," or "in other embodiments," which may each refer to one or more of the same or different embodiments in accordance with the present disclosure.

Various embodiments of the present disclosure provide electrosurgical systems and instruments suitable for sealing, cauterizing, coagulating/desiccating and/or cutting vessels and vascular tissue, ablating tissue, or otherwise modifying a tissue or organ of a patient, wherein the use of the presently-disclosed heat-sensitive agent, which is adapted to be visually observable and/or ascertainable in an ultrasound image (or other medical image), may provide feedback to allow the surgeon to selectively position the energy applicator in tissue during a procedure, and/or may allow the surgeon to adjust, as necessary, of the amount of energy delivered to tissue to facilitate effective execution of a procedure, e.g., an ablation procedure.

Various embodiments of the presently-disclosed electrosurgical systems and instruments use heat-distribution information provided by application of the presently-disclosed heat-sensitive agent. In accordance with embodiments of the present disclosure, a configuration of one or more heat-sensitive agents and/or drug agents(s) provides a well-organized shape (e.g., linear shape and/or curved shape) and/or pattern (e.g., regular, geometric pattern) adapted to be visually observable and/or ascertainable in an ultrasound image (or other medical image), e.g., to allow assessment of ablation margins and/or the rate of ablation and/or desiccation of tissue. Embodiments may be implemented using energy at RF or microwave frequencies or at other frequencies.

In accordance with embodiments of the present disclosure, one or more operating parameters of an electrosurgical power generating source are adjusted and/or controlled based on the heat-distribution information provided by the presently-disclosed heat-sensitive agent, e.g., to maintain a proper ablation rate, or to determine when tissue has been completely desiccated and/or the procedure has been completed.

During a procedure, such as an ablation or other heat treatment procedure, heat may not be uniformly distributed, such as at interfaces having different tissue properties, and accurate monitoring of, the ablation may require multi-point measurements of temperature distribution. The presently-disclosed heat-sensitive agent may be inserted into or placed adjacent to tissue in a variety of configurations, e.g., to allow visual assessment of ablation margins, or to allow the surgeon to determine the rate of ablation and/or when the procedure has been completed, and/or to trigger safety procedures and/or controls, e.g., controls that reduce power level and/or shut off the power delivery to the energy applicator.

Various embodiments of the presently-disclosed electrosurgical systems use heat-distribution information provided by the presently-disclosed heat-sensitive agent, which is adapted to be visually observable and/or ascertainable in an ultrasound image (or other medical image), to trigger safety procedures and/or controls, e.g., controls that reduce power level and/or shuts off the power delivery to the energy applicator, e.g., based on the tissue ablation rate and/or assessment of the ablation margins.

FIG. 1 schematically illustrates a monopolar electrosurgical system (shown generally as 1) configured to selectively apply electrosurgical energy to target tissue of a patient P. Electrosurgical system 1 generally includes a handpiece 2 coupled via a transmission line 4 to an electrosurgical power generating source 20. Handpiece 2 includes a surgical instrument 14 having one or more electrodes for treating tissue of the patient P (e.g., electrosurgical pencil, electrosurgical cutting probe, ablation electrode(s), etc.). In some embodiments, as shown in FIG. 1, the handpiece 2 includes a control assembly 30. When the electrosurgical energy is applied, the energy travels from the active electrode, to the surgical site, through the patient P and to a return electrode 6 (e.g., a plate positioned on the patient's thigh or back).

Electrosurgical energy is supplied to the instrument 14 by the electrosurgical power generating source 20. Power generating source 20 may be any generator suitable for use with electrosurgical devices to generate energy having a controllable frequency and power level, and may be configured to provide various frequencies of electromagnetic energy. Power generating source 20 may be configured to operate in a variety of modes, such as ablation, monopolar and bipolar cutting, coagulation, and other modes. Control assembly 30 may include a variety of mechanisms adapted to generate signals for adjusting and/or controlling one or more operating parameters (e.g., temperature, impedance, power, current, voltage, mode of operation, and/or duration of application of electromagnetic energy) of the electrosurgical power generating source 20.

The instrument 14 is electrically-coupled via a transmission line, e.g., supply line 4, to an active terminal 23 of the electrosurgical power generating source 20, allowing the instrument 14 to coagulate, ablate and/or otherwise treat tissue. The energy is returned to the electrosurgical power generating source 20 through the return electrode 6 via a transmission line, e.g., return line 8, which is connected to a return terminal 22 of the power generating source 20. In some embodiments, the active terminal 23 and the return terminal 22 may be configured to interface with plugs (not shown) associated with the instrument 14 and the return electrode 6, respectively, e.g., disposed at the ends of the supply line 4 and the return line 8, respectively.

The system 1 may include a plurality of return electrodes 6 that are arranged to minimize the chances of tissue damage by maximizing the overall contact area with the patient P. The power generating source 20 and the return electrode 6 may additionally, or alternatively, be configured for monitoring so-called "tissue-to-patient" contact to ensure that sufficient contact exists therebetween to further minimize chances of tissue damage. The active electrode may be used to operate in a liquid environment, wherein the tissue is submerged in an electrolyte solution.

Figure 2:
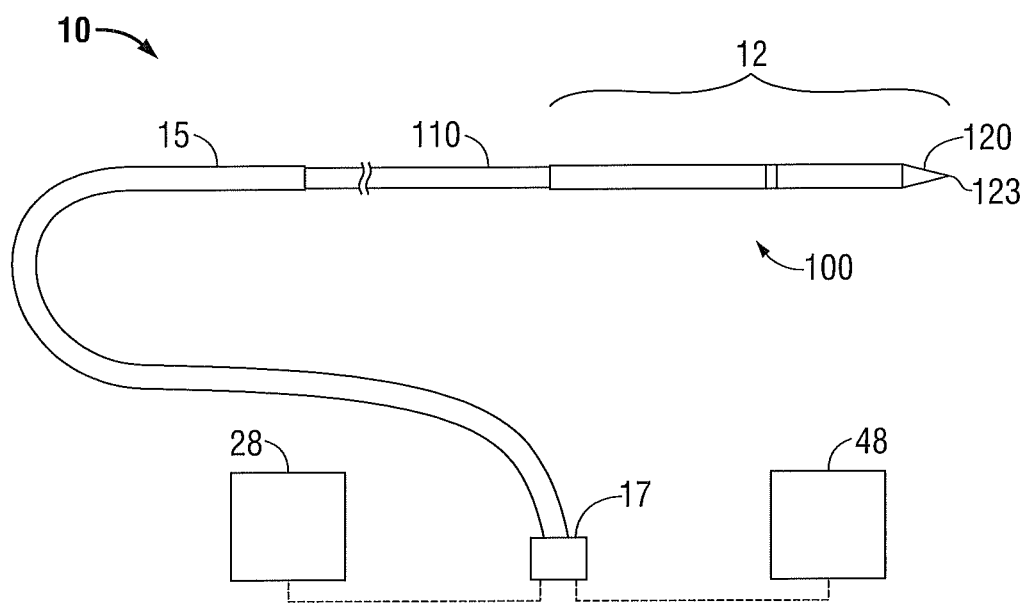
FIG. 2 is a schematic diagram of another embodiment of an electrosurgical system according to the present disclosure.

FIG. 2 schematically illustrates an electrosurgical system (shown generally as 10) including an energy applicator or probe 100. Probe 100 generally includes an antenna assembly 12, and may include a feedline (or shaft) 110 coupled to the antenna assembly 12. Located at the distal end of the antenna assembly 12 is an end cap or tapered portion 120, which may terminate in a sharp tip 123 to allow for insertion into tissue with minimal resistance. Feedline 110 may include a coaxial cable, which may be semi-rigid or flexible. A transmission line 15 may be provided to electrically couple the feedline 110 to an electrosurgical power generating source 28, e.g., a microwave or RF electrosurgical generator.

Feedline 110 may be cooled by fluid, e.g., saline or water, to improve power handling, and may include a stainless steel catheter. Transmission line 15 may additionally, or alternatively, provide a conduit (not shown) configured to provide coolant from a coolant source 18 to the probe 100. In some embodiments, as shown in FIG. 2, the feedline 110 is coupled via a transmission line 15 to a connector 17, which further operably connects the probe 100 to the electrosurgical power generating source 28. Power generating source 28 may be any generator suitable for use with electrosurgical devices, and may be configured to provide various frequencies of energy.

During microwave ablation, e.g., using the electrosurgical system 10, the probe 100 is inserted into or placed adjacent to tissue and microwave energy is supplied thereto. One or more linear-shaped (and/or curve-shaped) portions of a heat-sensitive agent or agents, which are described in more detail later in this description, may be positioned relative to the probe 100 (and/or relative to a target tissue). Probe 100 may be placed percutaneously or atop tissue, e.g., using conventional surgical techniques by surgical staff. A plurality of probes 100 may be placed in variously arranged configurations to substantially simultaneously ablate a target tissue, making faster procedures possible. Ablation volume is correlated with antenna design, antenna performance, number of energy applicators used simultaneously, ablation time and wattage, and tissue characteristics, e.g., tissue impedance.

Figure 3:
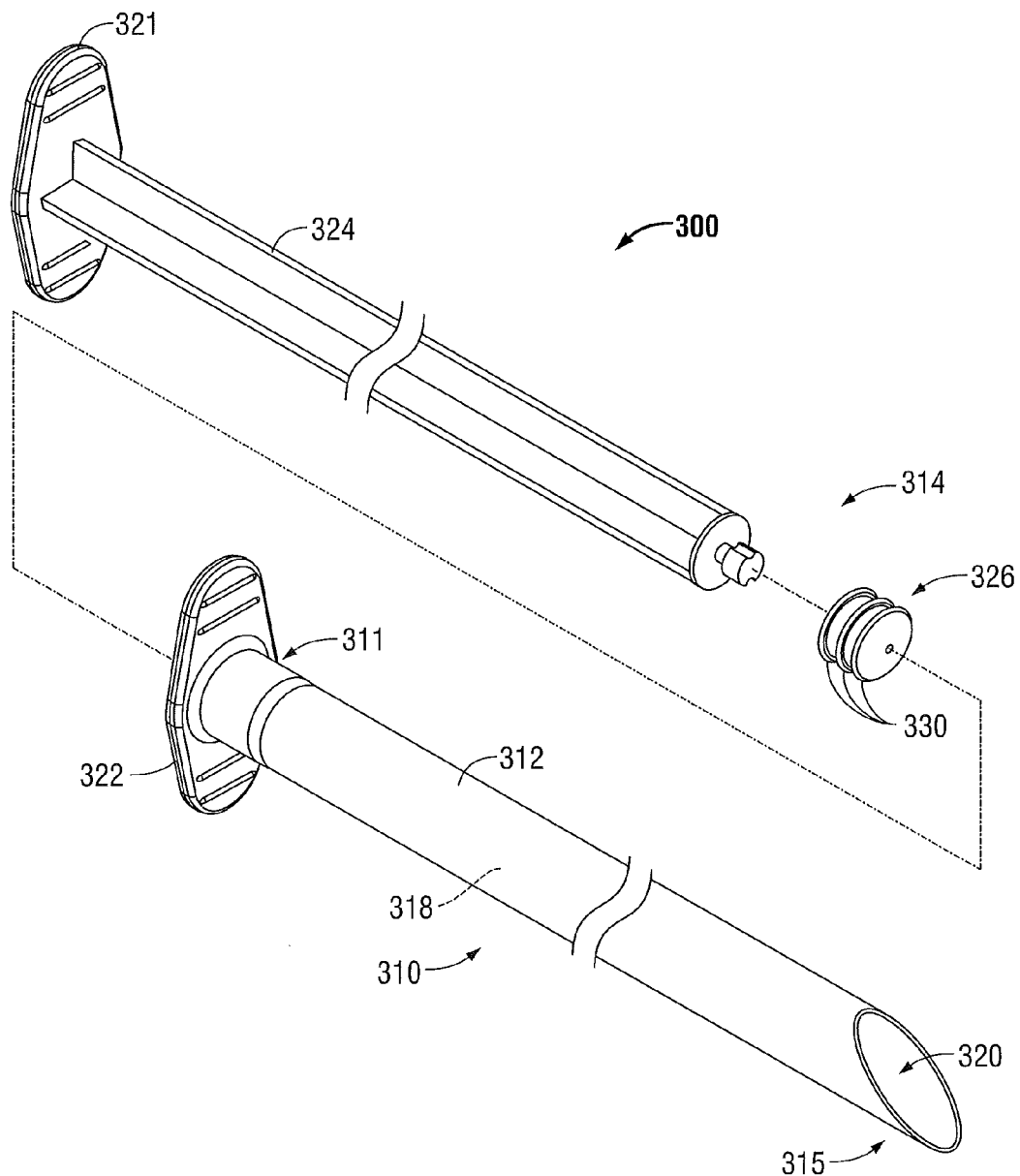
FIG. 3 is an enlarged, perspective view of an injection device adapted for the delivery of a material, e.g., a heat-sensitive agent, into tissue, the device including a housing and a plunger assembly, according to an embodiment of the present disclosure.

FIG. 3 shows an injection device (shown generally as 300) adapted for delivery of a heat-sensitive agent or agents, a drug agent or agents, or combinations thereof, into tissue according to an embodiment of the present disclosure. In some embodiments, the injection device 300 may be adapted to deliver a linearly-shaped portion and/or a curvilinear-shaped portion of a material, which may include heat-sensitive agent(s) and/or drug agent(s).

Injection device 300 generally includes a housing 310 and a plunger assembly 314. Housing 310 includes an elongated tubular body 312 defining a proximal end 311 and a distal end 315. Body 312 may have any suitable dimensions, e.g., length. Body 312 defines a chamber or fluid reservoir 318 therein. In some embodiments, as shown in FIG. 3, the housing 310 includes a slanted opening 320 disposed at the distal end 315 of the body 312. In some embodiments, as shown in FIG. 3, a flange 322 is disposed at the proximal end 311 of the body 312.

Body 312 may include any suitable material. In some embodiments, the body 312 is made of plastic, e.g., transparent polypropylene. Body 312 may be constructed of nearly any polymeric or glass material. In some embodiments, the body 312, or portion thereof, and/or the plunger assembly 314, or portion thereof, may be formed of a flexible material or materials, e.g., to allow delivery of one or more curvilinear-shaped (and/or linearly-shaped) portions of a heat-sensitive agent or agents (and/or medicament) into tissue.

Plunger assembly 314 is adapted to be mountable in the fluid reservoir 318 of the body 312 and moveable with respect to the housing 310. Plunger assembly 314 includes a plunger rod 324, and may include a flange 321 disposed at the proximal end of the plunger rod 324. Plunger rod 324 may include a plurality of vanes extending outwardly from a center longitudinal axis and extending at substantially right angles to each other. Plunger rod 324 may include any suitable material, e.g., plastic.

Fluid reservoir 318 may be configured to contain a predetermined volume of a heat-sensitive agent or agents, a drug agent or agents, or combinations thereof. In some embodiments, the fluid reservoir 318 may have an internal volume in the range of about 0.5 ml (milliliters) to about 100 ml.

In some embodiments, as shown in FIG. 3, the plunger assembly 314 includes a sealing member 326. Sealing member 326 is configured to be slideably received within the fluid reservoir 318 of the body 312, and may include one or more annular ribs 330 that sealingly engage an inner wall of the body 312 defining reservoir 318. Sealing member 326 may include any suitable material. In some embodiments, the sealing member 326 is formed from an elastomeric material.

Although the housing 310 shown in FIG. 3 has a generally tubular shape, it is to be understood that housing embodiments may have any suitable cross-sectional configuration. In some embodiments, the housing 310 may include a body 312 having a rectangular, triangular, or polygonal shape. In some embodiments, the housing 310 may include an opening 320 that is rectangular, triangular, octagonal or oval shaped.

In some embodiments, the injection device 300 may be configured as a single-use, auto-disable injection device. In alternative embodiments not shown, the injection device may include a driver mechanism, e.g., compressed gas, for imparting movement to the plunger assembly 314.

Figure 4:
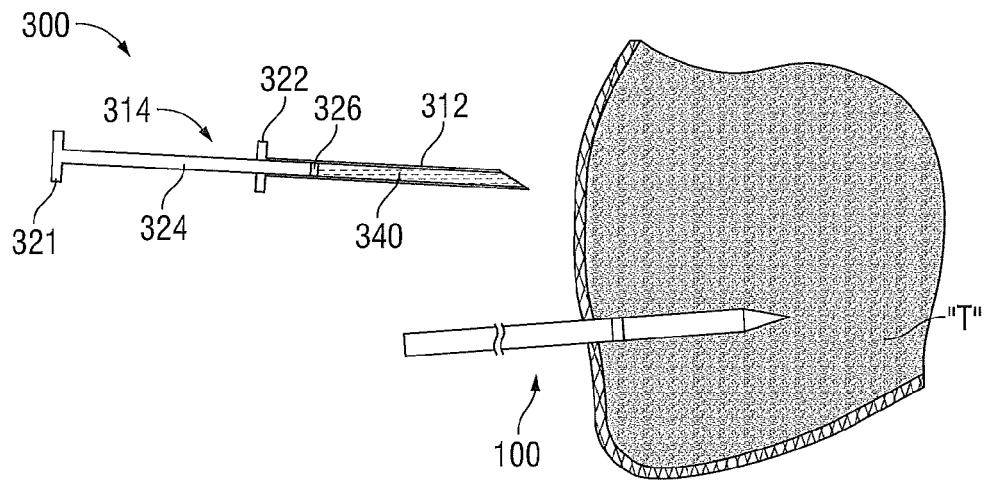
FIG. 4 is an enlarged, cross-sectional view of the energy applicator of FIG. 2 positioned for delivery of energy to a target tissue, shown with the injection device of FIG. 3 having a material, e.g., a heat-sensitive agent, disposed within the housing according to an embodiment of the present disclosure.
Figure 5:
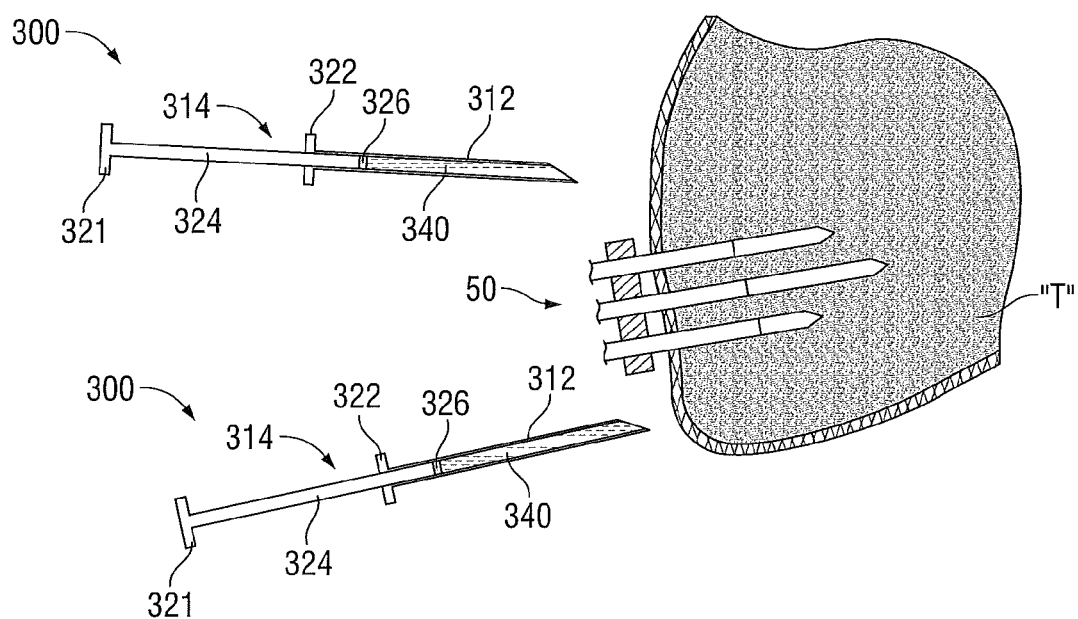
FIG. 5 is an enlarged, cross-sectional view of an energy applicator array positioned for delivery of energy to a target tissue, shown with two injection devices of FIG. 3 having a material, e.g., a heat-sensitive agent, disposed within the housing according to an embodiment of the present disclosure.
Figure 6:
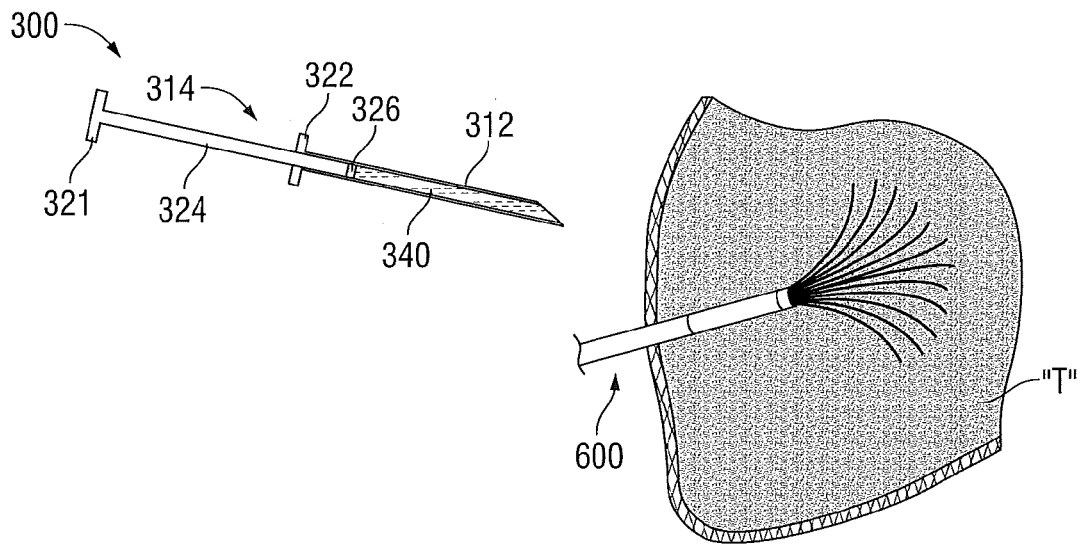
FIG. 6 is an enlarged, cross-sectional view of an RF ablation device positioned for delivery of energy to a target tissue, shown with the injection device of FIG. 3 having a material, e.g., a heat-sensitive agent, disposed within the housing according to an embodiment of the present disclosure.

In FIGS. 4 through 6, the injection device 300 of FIG. 3 is shown provided with a material 340 disposed within the fluid reservoir 318 of the body 312, prior to placement of the injection device 300 into a target tissue "T". In FIGS. 4 through 6, the housing 310 and the plunger assembly 314 of the injection device 300 are shown disposed in a first configuration, e.g., wherein the plunger assembly 314 is disposed in a retracted position.

Material 340 disposed within the fluid reservoir 318 may include one or more heat-sensitive agents, e.g., adapted to change echogenic properties in response to heat generated as a result of energy transmitted to the target tissue "T". The material 340 may exhibit change in its material properties and/or echogenic properties in response to received heat above a certain threshold value. The heat-sensitive agent's response to heat may be reversible, e.g., echogenic and/or material properties return to non-heated configuration when cooled down. The heat-sensitive agent's response to heat may be non-reversible, e.g., medium remains modified and/or transformed after heat is dissipated. In some embodiments, the material 340 may additionally, or alternatively, include one or more drug agents.

In FIG. 4, the energy applicator 100 of FIG. 2 is shown positioned for the delivery of energy to target tissue "T", and the injection device 300 is shown located outside of the target tissue "T", e.g., positioned for insertion thereinto.

Although a single injection device 300 is shown in FIG. 4, it is to be understood that any suitable number of injection devices 300 may be used, e.g., to provide a well-organized shape (e.g., linear shape and/or curved shape) and/or pattern (e.g., regular, geometric pattern) of a heat-sensitive agent or agents and/or a drug agent or drug agents, which may be visually observable and/or ascertainable in an ultrasound image (or other medical image).

In FIG. 5, an energy applicator array 50, which is described later in this description, is shown positioned for the delivery of energy to a target tissue "T", and two injection devices 300 are shown located outside of the target tissue "T", e.g., positioned for insertion thereinto.

In FIG. 6, an RF ablation device 600 is shown positioned for delivery of energy to a target tissue "T", and an injection device 300 is located outside of the target tissue "T", e.g., positioned for insertion thereinto. For ease of explanation and understanding, a single injection device 300 is described with respect to FIGS. 6 through 9; however, any suitable number of the injection devices 300 may be used. A variety of medical imaging modalities, e.g., computed tomography (CT) scan or ultrasound, may be used to guide the RF ablation device 600 and/or injection device 300 into the area of tissue "T" to be treated.

Figure 7:
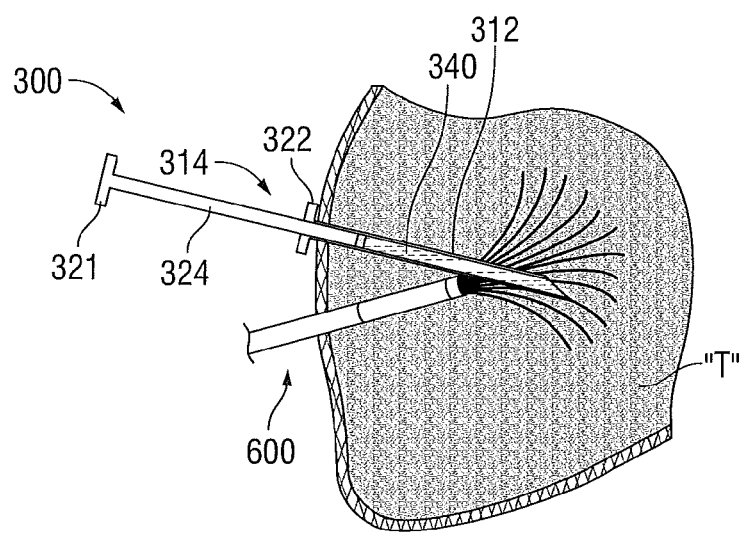
FIG. 7 is an enlarged, cross-sectional view of the injection device of FIG. 3 shown disposed, in part, within a target tissue, e.g., positioned relative to the RF ablation device and/or in relation to the target tissue of FIG. 6, shown with the housing and the plunger assembly of the injection device disposed in a first configuration according to an embodiment of the present disclosure.

In FIG. 7, the injection device 300 of FIG. 3, provided with material 340 disposed within the fluid reservoir 318, is shown disposed, in part, within the target tissue "T", e.g., positioned relative to the RF ablation device 600 and/or in relation to the target tissue "T" of FIG. 6, prior to delivery of the material 340 into the target tissue "T".

Figure 8A:
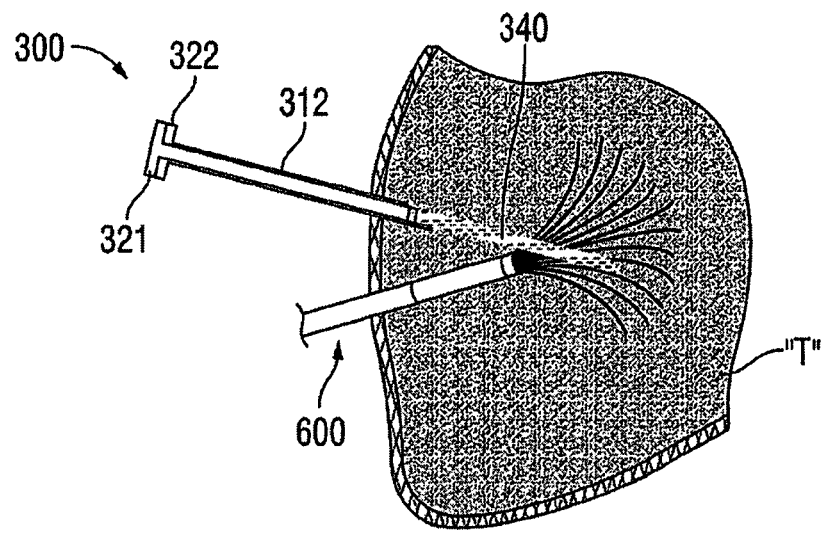
FIG. 8A is an enlarged, cross-sectional view of the injection device of FIG. 3 shown disposed, in part, within the target tissue of FIG. 7, shown with the housing and the plunger assembly disposed in a second configuration, upon the delivery of a linearly-shaped portion of a material, e.g., a heat-sensitive agent, into the target tissue, according to an embodiment of the present disclosure.

In FIG. 8A, the injection device of FIG. 7 is shown disposed, in part, within the target tissue, shown with the housing 310 and the plunger assembly 314 disposed in a second configuration, e.g., wherein the plunger assembly 314 is disposed in an advanced position, upon the delivery of a linear-shaped volume of the material 340, e.g., in proximity to the RF ablation device 600.

Figure 8B:
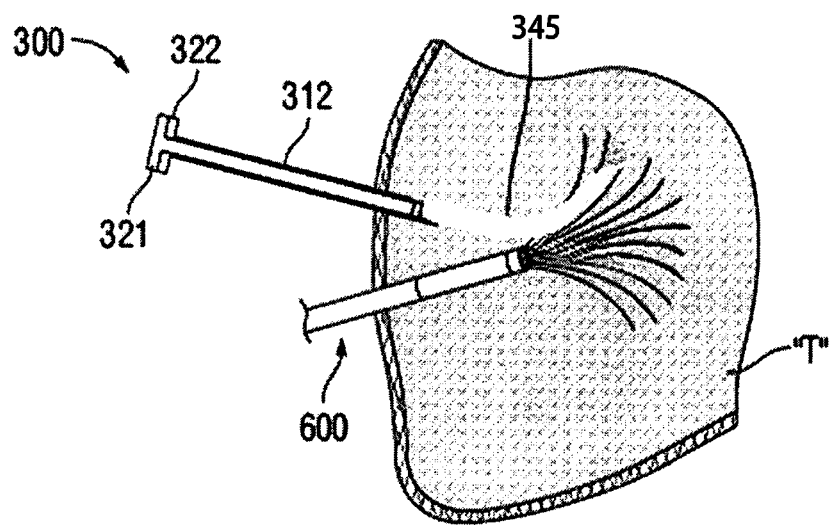
FIG. 8B is an enlarged, cross-sectional view of the injection device of FIG. 3 shown disposed, in part, within the target tissue of FIG. 7, shown with the housing and the plunger assembly disposed in a second configuration, upon the delivery of a curvilinear-shaped portion of a material, e.g., a heat-sensitive agent, into the target tissue, according to an embodiment of the present disclosure.

In FIG. 8B the injection device of FIG. 7 is shown disposed, in part, within the target tissue, shown with the housing 310 and the plunger assembly 314 disposed in a second configuration, e.g., wherein the plunger assembly 314 is disposed in an advanced position, upon the delivery of a curvilinear-shaped volume of the material 345, e.g., in proximity to the RF ablation device 600.

Figure 9:
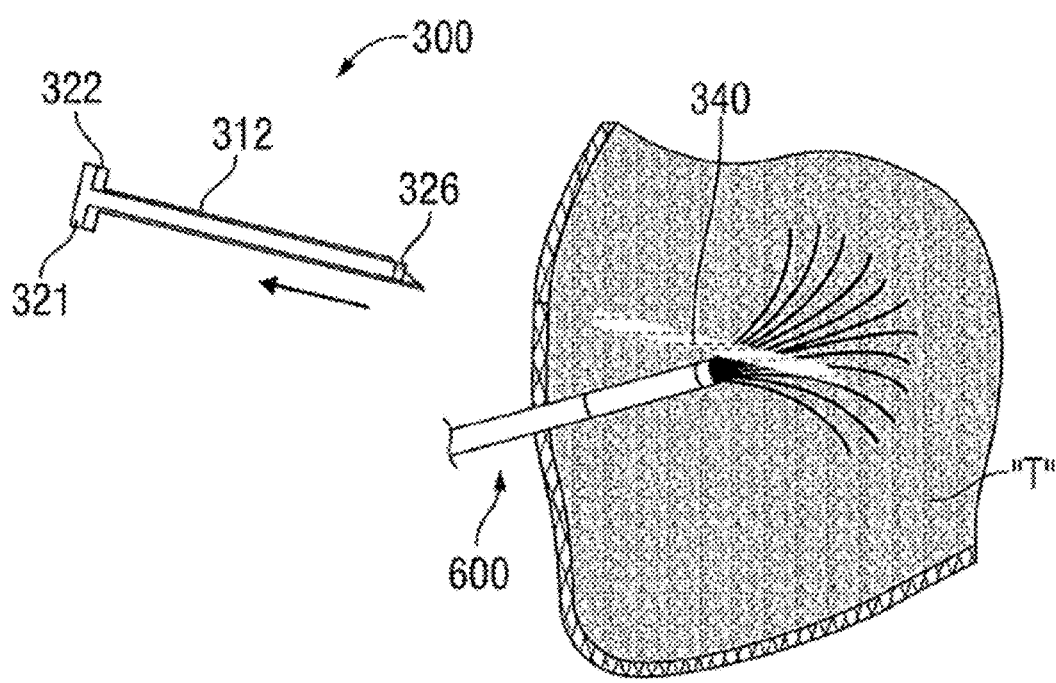
FIG. 9 is an enlarged, cross-sectional view of the target tissue of FIG. 8A, shown with the linear-shaped portion of the material, e.g., a heat-sensitive agent, positioned relative to the RF ablation device and/or in relation to the target tissue, shown with injection device after withdrawal thereof from the target tissue according to an embodiment of the present disclosure.

FIG. 9 is an enlarged, cross-sectional view of the injection device of FIG. 3, after the removal of the injection device from the target tissue of FIG. 8A, shown with the linear-shaped portion of the heat-sensitive agent disposed within the target tissue according to an embodiment of the present disclosure. In some embodiments, the housing 310 is moved proximally to dispense the linear-shaped volume of the material 340 from within the fluid reservoir 318 into the target tissue "T". In some embodiments, as shown in FIG. 9, wherein a flange 322 is disposed at the proximal end of the body 312 and a flange 321 is disposed at the proximal end of the plunger rod 324, the injection device 300 may be adapted to fully dispense the material 340 from within the fluid reservoir 318 when the flange 322 associated with the body 312 is brought into contact with the flange 321 associated with the plunger rod 324.

The visual assistance provided by the utilization of the presently-disclosed material 340 configured as a well-organized shape (e.g., linear shape and/or curved shape) and/or pattern (e.g., regular, geometric pattern) by providing heat-distribution information on a display device may allow the surgeon to selectively position the energy applicator (e.g., probe 100 shown in FIG. 4, energy applicator array 50 shown in FIGS. 5 and 11, or RF ablation device 600 shown in FIGS. 6-9) in tissue, and/or may allow the surgeon to monitor and adjust, as necessary, the amount of energy delivered to tissue, such as to facilitate effective execution of a procedure, e.g., an ablation procedure.

Figure 10:
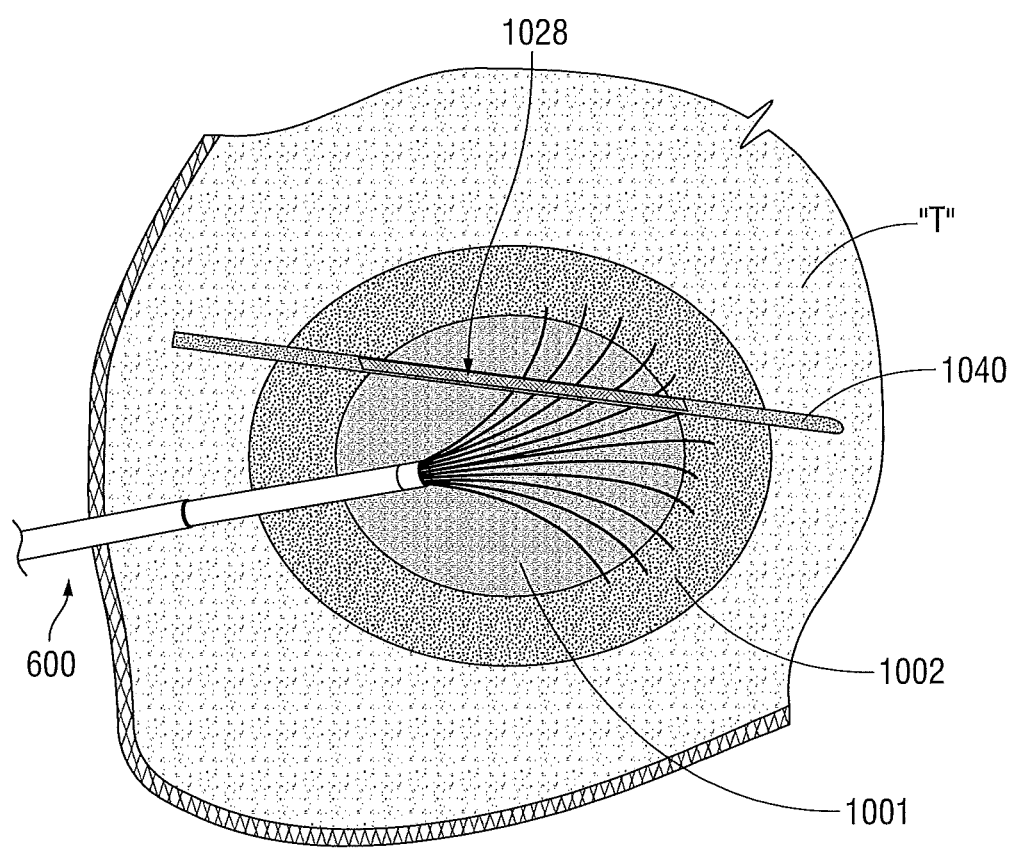
FIG. 10 is a diagrammatic representation of a tissue region, including normal tissue to a region of thermal damage, shown with the energy delivery device of FIG. 7 and a linearly-shaped portion of material, e.g., a heat-sensitive agent, according to an embodiment of the present disclosure.

FIG. 10 is a diagrammatic representation of a region tissue of "T" shown with a material 1040 disposed in proximity to the RF ablation device 600. Material 1040 is similar to the material 340 shown in FIG. 9 and further description thereof is omitted in the interests of brevity. Although, in the illustrative example shown in FIG. 10, the tissue "T" includes first and second zones of thermal damage 1001 and 1002, respectively, it is to be understood that any number of zones of thermal damage may result from the ablation or other heat-treatment procedure.

As shown in FIG. 10, in response to ablation or other heat-treatment procedure, a portion 1028 of the material 1040 exhibits change in material properties and/or echogenic properties, as compared to other portions of the material 1040 adjacent thereto. In alternative embodiments not shown, one or more portions of the material 1040, e.g., portions disposed within the second zone 1002, may additionally, or alternatively, exhibit change in material properties and/or echogenic properties, e.g., depending on the material properties of the material 1040 and/or the change in temperature by a certain amount in the second zone 1002.

Figure 11:
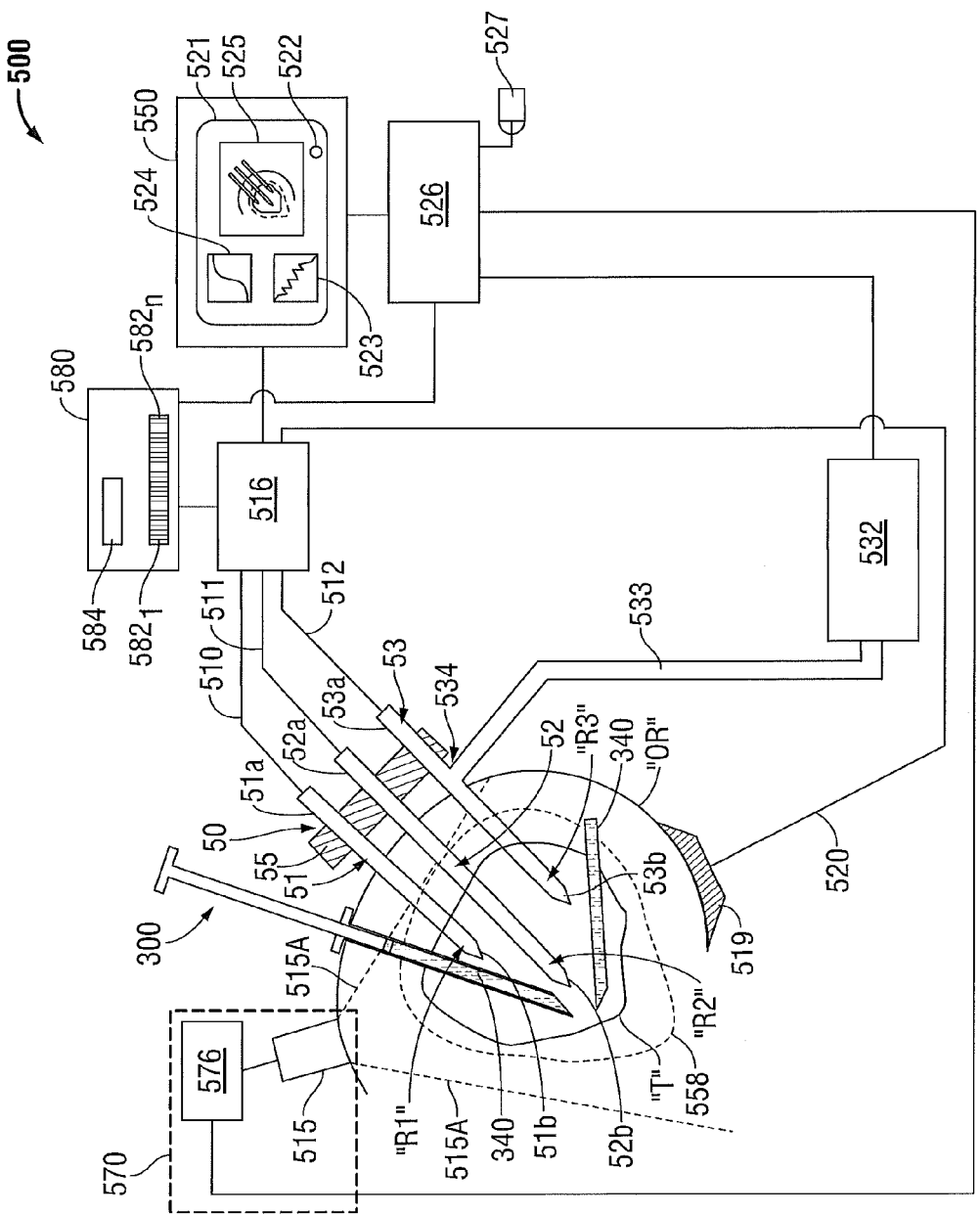
FIG. 11 is a schematic diagram of an electrosurgical system shown with the injection device of FIG. 3, shown with the energy applicator array of FIG. 5 positioned for the delivery of energy to target tissue, according to an embodiment of the present disclosure.

FIG. 11 schematically illustrates an electrosurgical system (shown generally as 500) according to an embodiment of the present disclosure that includes an electromagnetic energy delivery device or energy applicator array 50 positioned for the delivery of energy to a target tissue "T". Energy applicator array 50 may include one or more energy applicators or probes.

In some embodiments, as shown in FIG. 11, the electrosurgical system 500 includes two material 340 portions, e.g., positioned relative to the energy applicator array 50 and/or in relation to the target tissue "T". It is to be understood that any suitable number of the injection device 300 may be used. The relative positioning of the material 340 portions may be varied from the configuration depicted in FIG. 10.

In the embodiment shown in FIG. 10, the energy applicator array 50 includes three probes 51, 52 and 53 having different lengths and arranged substantially parallel to each other. The probes may have similar or different diameters, may extend to equal or different lengths, and may have a distal end with a tapered tip. In some embodiments, the probe(s) may be provided with a coolant chamber, and may be integrally associated with a hub (e.g., hub 534 shown in FIG. 10) that provides electrical and/or coolant connections to the probe(s). Additionally, or alternatively, the probe(s) may include coolant inflow and outflow ports to facilitate the flow of coolant into, and out of, the coolant chamber.

Probes 51, 52 and 53 generally include a radiating section "R1", "R2" and "R3", respectively, operably connected by a feedline (or shaft) 51a, 52a and 53a, respectively, to an electrosurgical power generating source 516, e.g., a microwave or RF electrosurgical generator. In some embodiments, the power generating source 516 is configured to provide microwave energy at an operational frequency from about 300 MHz to about 10 GHz. Power generating source 516 may be configured to provide various frequencies of electromagnetic energy.

Transmission lines 510, 511 and 512 may be provided to electrically couple the feedlines 51a, 52a and 53a, respectively, to the electrosurgical power generating source 516. Located at the distal end of each probe 51, 52 and 53 is a tip portion 51b, 52b and 53b, respectively, which may be configured to be inserted into an organ "OR" of a human body or any other body tissue. Tip portion 51b, 52b and 53b may terminate in a sharp tip to allow for insertion into tissue with minimal resistance. The shape, size and number of probes of the energy applicator array 50 may be varied from the configuration depicted in FIG. 10.

Electrosurgical system 500 according to embodiments of the present disclosure includes a user interface 550. User interface 550 may include a display device 521, such as without limitation a flat panel graphic LCD (liquid crystal display), adapted to visually display one or more user interface elements (e.g., 523, 524 and 525 shown in FIG. 10). In an embodiment, the display device 521 includes touchscreen capability, e.g., the ability to receive user input through direct physical interaction with the display device 521, e.g., by contacting the display panel of the display device 521 with a stylus or fingertip.

User interface 550 may additionally, or alternatively, include one or more controls 522 that may include without limitation a switch (e.g., pushbutton switch, toggle switch, slide switch) and/or a continuous actuator (e.g., rotary or linear potentiometer, rotary or linear encoder). In an embodiment, a control 522 has a dedicated function, e.g., display contrast, power on/off, and the like. Control 522 may also have a function that may vary in accordance with an operational mode of the electrosurgical system 500. A user interface element (e.g., 523 shown in FIG. 10) may be provided to indicate the function of the control 522.

As shown in FIG. 10, the electrosurgical system 500 may include a reference electrode 519 (also referred to herein as a "return" electrode). Return electrode 519 may be electrically coupled via a transmission line 520 to the power generating source 516. During a procedure, the return electrode 519 may be positioned in contact with the skin of the patient or a surface of the organ "OR". When the surgeon activates the energy applicator array 50, the return electrode 519 and the transmission line 520 may serve as a return current path for the current flowing from the power generating source 516 through the probes 51, 52 and 53.

During microwave ablation, e.g., using the electrosurgical system 500, the energy applicator array "E" is inserted into or placed adjacent to tissue and microwave energy is supplied thereto. Ultrasound or computed tomography (CT) guidance may be used to accurately guide the energy applicator array 50 into the area of tissue to be treated. A clinician may pre-determine the length of time that microwave energy is to be applied. Application duration may depend on a variety of factors such as energy applicator design, number of energy applicators used simultaneously, tumor size and location, and whether the tumor was a secondary or primary cancer. The duration of microwave energy application using the energy applicator array 50 may depend on the progress of the heat distribution within the tissue area that is to be destroyed and/or the surrounding tissue.

FIG. 10 shows a target tissue including ablation target tissue represented in sectional view by the solid line "T". It may be desirable to ablate the target tissue "T" by fully engulfing the target tissue "T" in a volume of lethal heat elevation. Target tissue "T" may be, for example, a tumor that has been detected by a medical imaging system 570.

Medical imaging system 570, according to various embodiments, includes one or more image acquisition devices (e.g., scanner 515 shown in FIG. 10) of any suitable imaging modality. Medical imaging system 570 may additionally, or alternatively, include a medical imager (not shown) operable to form a visible representation of the image based on the input pixel data. Medical imaging system 570 may include a computer-readable storage medium such as an internal memory unit 576, which may include an internal memory card and removable memory, capable of storing image data representative of an ultrasound image (and/or images from other modalities) received from the scanner 515. In some embodiments, the medical imaging system 570 may be a multi-modal imaging system capable of scanning using different modalities. Medical imaging system 570, according to embodiments of the present disclosure, may include any device capable of generating digital data representing an anatomical region of interest.

Image data representative of one or more images may be communicated between the medical imaging system 570 and a processor unit 526. Medical imaging system 570 and the processor unit 526 may utilize wired communication and/or wireless communication. Processor unit 526 may include any type of computing device, computational circuit, or any type of processor or processing circuit capable of executing a series of instructions that are stored in a computer-readable storage medium (not shown), which may be any device or medium that can store code and/or data. Processor unit 526 may be adapted to run an operating system platform and application programs. Processor unit 526 may receive user inputs from a keyboard (not shown), a pointing device 527, e.g., a mouse, joystick or trackball, and/or other device communicatively-coupled to the processor unit 526.

As shown in FIG. 10, a scanner 515 of any suitable imaging modality may be disposed in contact with the organ "OR" to provide image data. As an illustrative example, the two dashed lines 515A in FIG. 10 bound a region for examination by the scanner 515, e.g., a real-time ultrasonic scanner.

In FIG. 10, the dashed line 558 surrounding the target tissue "T" represents the ablation isotherm in a sectional view through the organ "OR". Such an ablation isotherm may be that of the surface achieving possible temperatures of approximately 50° C. or greater. The shape and size of the ablation isotherm volume, as illustrated by the dashed line 558, may be influenced by a variety of factors including the configuration of the energy applicator array 50, the geometry of the radiating sections "R1", "R2" and "R3", cooling of the probes 51, 52 and 53, ablation time and wattage, and tissue characteristics.

Processor unit 526 may be connected to one or more display devices (e.g., 521 shown in FIG. 10) for displaying output from the processor unit 26, which may be used by the clinician to visualize the target tissue "T", the ablation isotherm volume 558, and/or the material 340 in real-time, or near real-time, during a procedure, e.g., an ablation procedure.

In some embodiments, real-time data and/or near real-time data acquired from the medical imaging system 570 that includes heat-distribution information, e.g., data representative of one or more regions of the material 340 during an ablation procedure, may be outputted from the processor unit 526 to one or more display devices. Processor unit 526 is adapted to analyze image data including heat-distribution information to determine one or more parameters associated with the energy applicator array 50 and/or one or more parameters associated with the electrosurgical power generating source 516 e.g., based on the tissue ablation rate and/or assessment of the ablation margins.

Electrosurgical system 500 may include a library 580 including a plurality of material 340 profiles or overlays $582_1$-$582_n$. As it is used in this description, "library" generally refers to any repository, databank, database, cache, storage unit and the like. Each of the overlays $582_1$-$582_n$ may include a thermal profile that is characteristic of and/or specific to particular material 340 configurations, e.g., exposure time and/or the change in temperature by a certain amount.

Library 580 according to embodiments of the present disclosure may include a database 584 that is configured to store and retrieve energy applicator data, e.g., parameters associated with one or more energy applicators (e.g., 51, 52 and 53 shown in FIG. 10) and/or one or more energy applicator arrays (e.g., 50 shown in FIG. 10) and/or parameters associated with material 340. Images and/or non-graphical data stored in the library 580, and/or retrievable from a PACS database (not shown), may be used to configure the electrosurgical system 500 and/or control operations thereof. For example, heat-distribution information, e.g., data representative of material 340 and/or regions associated therewith during an ablation procedure, according to embodiments of the present disclosure, may be used as a feedback tool to control an instrument's and/or clinician's motion, e.g., to allow clinicians to avoid ablating certain structures, such as large vessels, healthy organs or vital membrane barriers.

Hereinafter, methods of directing energy to tissue are described with reference to FIGS. 12 and 13. It is to be understood that the steps of the methods provided herein may be performed in combination and in a different order than presented herein without departing from the scope of the disclosure.

Figure 12:
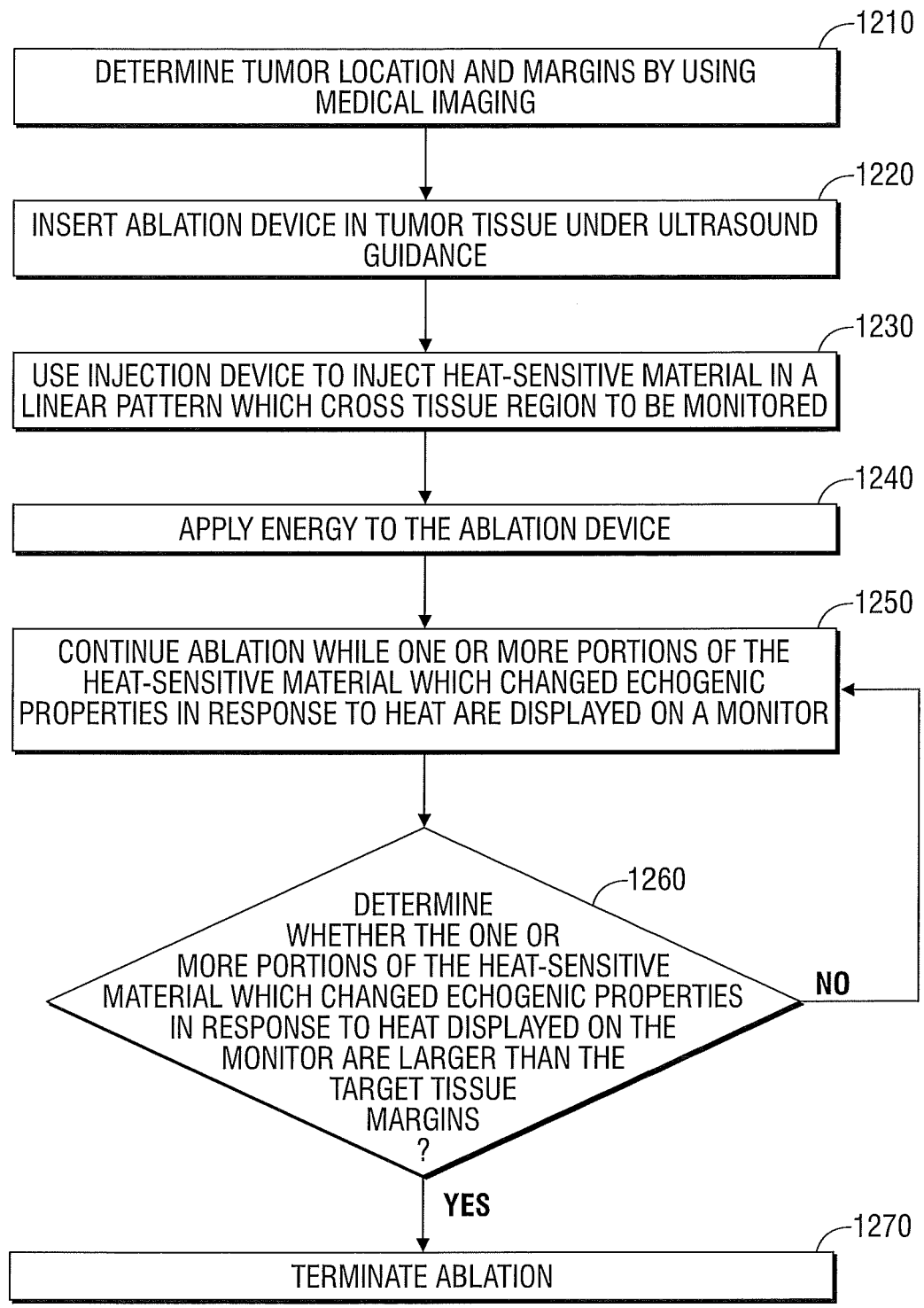
FIG. 12 is a flowchart illustrating a method of directing energy to tissue in accordance with an embodiment of the present disclosure.

FIG. 12 is a flowchart illustrating a method of directing energy to tissue according to an embodiment of the present disclosure. In step 1210, tumor "T" location and/or tumor "T" margins are determined. The target tissue location and target tissue margins may be determined by using medical imaging. Any suitable medical imaging techniques may be used, e.g., ultrasound, magnetic resonance imaging (MRI), or computed tomography (CT) imaging.

In step 1220, an ablation device 600 is inserted into tissue "T". Ultrasound guidance may be used to guide the ablation device 600 into the area of tissue "T" to be treated. The ablation device 600 is operably associated with an electrosurgical power generating source 516.

In step 1230, a material 340 having a shape is introduced into a tissue region "T" to be monitored. The material 340 is adapted to change echogenic properties in response to heat. The material 340 may include one or more heat-sensitive agents. In some embodiments, the material 340 may include heat-sensitive microbubbles, e.g., a core of liquid perfluorocarbon (PFC) compound and a shell of biodegradable poly lactic-co-glycolic acid (PLGA). The material 340 may include one or more drug agents. In some embodiments, the material 340 may include drug agents, e.g., chemotherapy drugs, encased in heat-sensitive microbubbles.

In step 1240, energy from the electrosurgical power generating source 516 is applied to the ablation device 600. The electrosurgical power generating source 516 may be capable of generating energy at RF or microwave frequencies or at other frequencies.

In step 1250, the material 340 is monitored on a monitor 521. In some embodiments, monitoring the material 340, in step 1250, includes continuing the ablation while one or more portions of the material 340 which changed echogenic properties in response to heat (e.g., portion 1028 shown in FIG. 10) are displayed on the monitor 521.

In step 1260, an echogenic response of the material 340 is determined. In some embodiments, determining the echogenic response of the material 340, in step 1260, includes determining whether one or more portions of the material 340, which changed echogenic properties in response to heat, displayed on the monitor 521 are larger than the target tissue margins determined in step 1210.

If it is determined, in step 1260, that the echogenic response of the material 340 is outside a predetermined target tissue threshold (e.g., one or more portions of the material 340 which changed echogenic properties in response to heat are larger than the target tissue margins determined in step 1210) then, ablation is terminated, in step 1270. Otherwise, if it is determined, in step 1260, that the echogenic response of the material 340 is below a predetermined target tissue threshold (e.g., one or more portions of the material 340 which changed echogenic properties in response to heat are not larger than the target tissue margins), then repeat step 1250.

Figure 13:
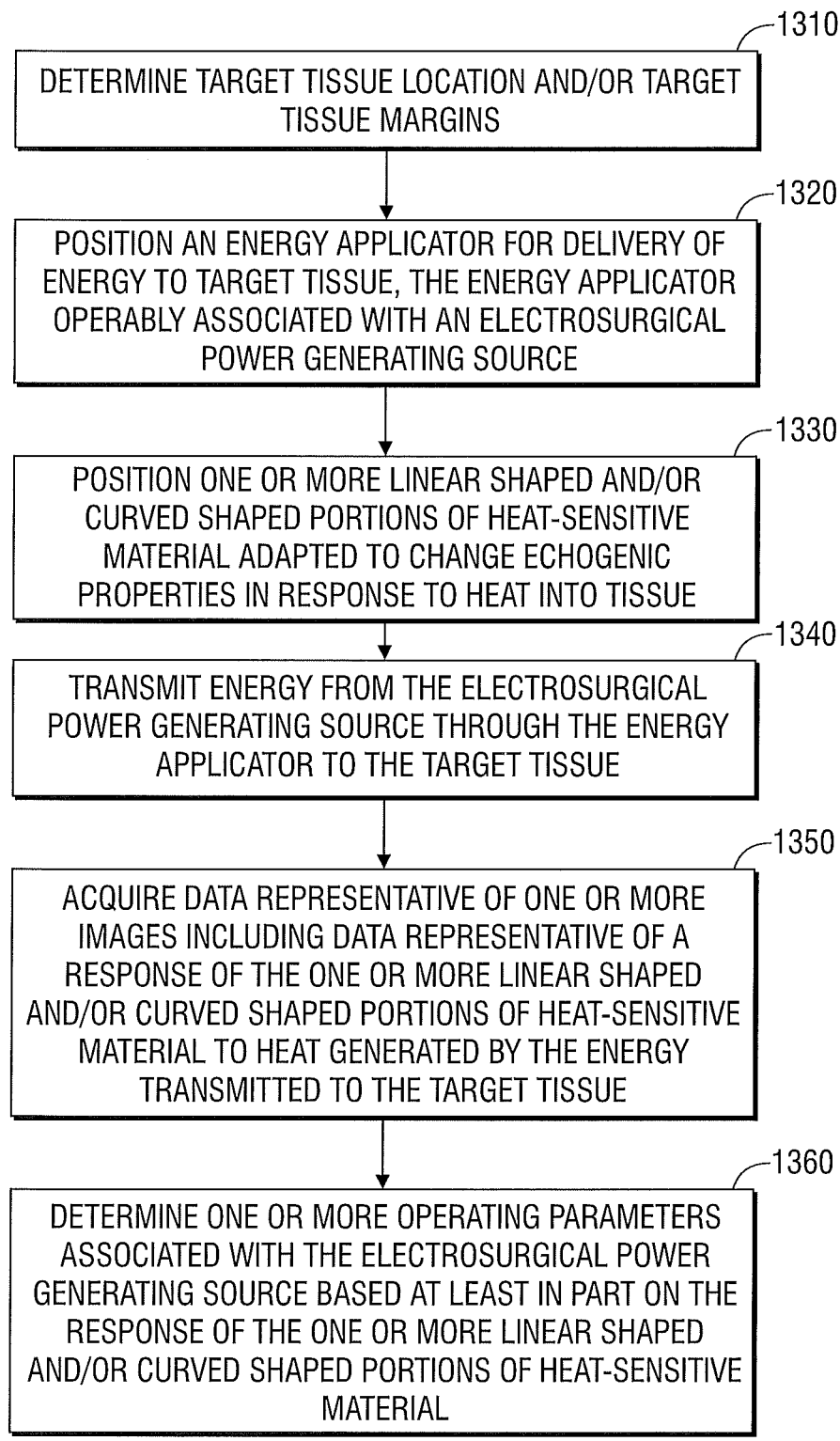
FIG. 13 is a flowchart illustrating a method of directing energy to tissue in accordance with another embodiment of the present disclosure.

FIG. 13 is a flowchart illustrating a method of directing energy to tissue according to an embodiment of the present disclosure. In step 1310, target tissue (e.g., tumor) "T" location and/or target tissue "T" margins are determined, e.g., by using medical imaging.

In step 1320, an energy applicator 600 is positioned for delivery of energy to target tissue "T". The energy applicator may be inserted directly into tissue "T", inserted through a lumen, e.g., a vein, needle or catheter, placed into the body during surgery by a clinician, or positioned in the body by other suitable methods. Ultrasound guidance may be used to guide the energy applicator 600 into the area of tissue "T" to be treated. The energy applicator 600 is operably associated with an electrosurgical power generating source 516.

In step 1330, one or more shaped portions of a heat-sensitive material 340 are positioned into tissue "T". The heat-sensitive material 340 is adapted to change echogenic properties in response to heat. In some embodiments, the heat-sensitive material 340 may include heat-sensitive microbubbles. In some embodiments, the heat-sensitive material 340 may include one or more drug agents.

In step 1340, energy from the electrosurgical power generating source 516 is transmitted through the energy applicator 600 to the target tissue "T". The electrosurgical power generating source 516 may be capable of generating energy at RF or microwave frequencies or at other frequencies.

In step 1350, data representative of one or more images including data representative of a response of one or more shaped portions of the heat-sensitive material to the heat generated by the energy transmitted to the target tissue is acquired.

In step 1360, one or more operating parameters associated with the electrosurgical power generating source 516 are determined based at least in part on response of one or more shaped portions of the heat-sensitive material to the heat generated by the energy transmitted to the target tissue. Some examples of operating parameters associated with an electrosurgical power generating source 516 that may be determined include temperature, impedance, power, current, voltage, mode of operation, and duration of application of electromagnetic energy.

In some embodiments, safety procedures and/or controls, e.g., controls that reduce power level and/or shut off the power delivery to the energy applicator, may be triggered based on the tissue ablation rate and/or assessment of the ablation margins. In some embodiments, a processor unit 526 configured to generate one or more electrical signals for controlling one or more operating parameters associated with an electrosurgical power generating source 516 may be adapted to reduce power level and/or shut off the power delivery based on the tissue ablation rate and/or the proximity of the margins of ablated tissue to the target tissue margins.

The above-described injection device for heat-sensitive agent (and/or drug agent) application, electrosurgical devices and systems, and methods of directing energy to target tissue may be suitable for various open and endoscopic surgical procedures.

The above-described heat-sensitive agent may be inserted into or placed adjacent to tissue in a variety of configurations, e.g., to allow visual assessment of ablation margins, or to allow the surgeon to determine the rate of ablation and/or when the procedure has been completed, and/or to trigger safety procedures and/or controls, e.g., controls that reduce power level and/or shuts off the power delivery to the energy applicator. The above-described injection device may be adapted to deliver a linearly-shaped portion and/or a curvilinear-shaped portion of a material, e.g., including a heat-sensitive agent or agents, a drug agent or agents, or combinations thereof.

The use of the above-described heat-sensitive agent, which is adapted to be visually observable and/or ascertainable in an ultrasound image (or other medical image), may provide feedback to allow the surgeon to selectively position the energy applicator in tissue during a procedure, and/or may allow the surgeon to adjust, as necessary, of the amount of energy delivered to tissue to facilitate effective execution of a procedure, e.g., an ablation procedure.

In the above-described embodiments, one or more operating parameters of an electrosurgical power generating source may be adjusted and/or controlled based on the heat-distribution information provided by the presently-disclosed heat-sensitive agent, e.g., to maintain a proper ablation rate, or to determine when tissue has been completely desiccated and/or the procedure has been completed.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method of directing energy to tissue, comprising:
   introducing a material having a shape into the tissue, the material possessing an echogenic property which changes in response to heat;
   applying energy to a tissue target within the tissue using an ablation device;
   measuring an echogenic property value representing the echogenic property of the material as the echogenic property value changes in response to heat generated from the application of energy;
   determining whether the echogenic property value surpasses a predetermined threshold; and
   terminating the application of energy if the echogenic property value surpasses the predetermined threshold.

2. The method of directing energy to tissue of claim 1, wherein the tissue target and the predetermined threshold are determined by using medical imaging.

3. The method of directing energy to tissue of claim 1, wherein the material includes at least one heat-sensitive agent.

4. The method of directing energy to tissue of claim 1, wherein the shape of the material is linear.

5. The method of directing energy to tissue of claim 1, wherein the shape of the material is curvilinear.

6. The method of directing energy to tissue of claim 1, wherein the material is introduced into the tissue using an injection device.

7. The method of directing energy to tissue of claim 6, wherein the injection device is adapted to deliver a linearly-shaped portion of the material.

8. The method of directing energy to tissue of claim 6, wherein the injection device is adapted to deliver a curvilinear-shaped portion of the material.

9. A method of directing energy to tissue, comprising:
   positioning at least one shaped portion of a heat-sensitive material into the tissue, the at least one shaped portion of the heat-sensitive material possessing an echogenic property which changes in response to heat;
   transmitting energy from an electrosurgical power generating source through an energy applicator to a tissue target within the tissue;
   acquiring data representative of the echogenic property of the at least one portion of the heat-sensitive material as the echogenic property changes in response to heat generated by the energy transmitted to the tissue target; and
   adjusting at least one operating parameter of the electrosurgical power generating source based at least in part on the acquired data.

10. The method of directing energy to tissue of claim 9, wherein the shape of the material is linear.

11. The method of directing energy to tissue of claim 9, wherein the shape of the material is curvilinear.

12. The method of directing energy to tissue of claim 9, wherein the at least one operating parameter associated with the electrosurgical power generating source is selected from the group consisting of temperature, impedance, power, current, voltage, mode of operation, and duration of application of electromagnetic energy.

13. The method of directing energy to tissue of claim 9, wherein the heat-sensitive material is introduced into the tissue using an injection device.

14. The method of directing energy to tissue of claim 13, wherein the injection device is adapted to deliver a linearly-shaped portion of the heat-sensitive material.

15. The method of directing energy to tissue of claim 13, wherein the injection device is adapted to deliver a curvilinear-shaped portion of the heat-sensitive material.

* * * * *